United States Patent [19]

Koizumi

[11] Patent Number: 5,145,673
[45] Date of Patent: Sep. 8, 1992

[54] QUENCHING AND DEODORIZING COMPOSITIONS

[75] Inventor: Kazuo Koizumi, Kobe, Japan

[73] Assignee: Ork Corporation, Osaka, Japan

[21] Appl. No.: 645,736

[22] Filed: Jan. 25, 1991

[30] Foreign Application Priority Data

Feb. 14, 1990 [JP] Japan .................................... 2-34956
Nov. 22, 1990 [JP] Japan .................................. 2-319940

[51] Int. Cl.⁵ ................................................. A61L 9/00
[52] U.S. Cl. .................... 424/76.1; 424/76.4; 424/76.9
[58] Field of Search ................. 424/78, 81, 76.1, 76.4, 424/76.9

[56] References Cited

U.S. PATENT DOCUMENTS

| | | | |
|---|---|---|---|
| 4,494,482 | 1/1985 | Arnold | 119/1 |
| 4,517,919 | 5/1985 | Benjamin et al. | 119/1 |
| 4,816,220 | 3/1989 | Roychowdhury | 422/5 |
| 4,939,030 | 7/1990 | Tsuji et al. | 428/315.5 |

*Primary Examiner*—Thurman K. Page
*Assistant Examiner*—Louis A. Piccone
*Attorney, Agent, or Firm*—Wenderoth, Lind & Ponack

[57] ABSTRACT

The gel liquid quenching and deodorizing compositions for cigarettes, which comprise water, a deodorizing agent, a water-absorbing polymer or thickener and a viscosity-imparting agent and exhibit excellent quenching and deodorizing effects for a long time are discussed. Due to their gel form, the compositions can offer effects in that they can be used in shaky vehicles and ashtrays can be cleaned easily after use by letting the content enveloped therein fall out.

7 Claims, No Drawings

QUENCHING AND DEODORIZING COMPOSITIONS

BACKGROUND OF THE INVENTION

This invention relates to quenching and deodorizing compositions, particularly, to gel liquid quenching and deodorizing compositions for cigarettes.

Cigarettes are generally quenched by rubbing out in an ash tray. However, sometimes it happens that quenching takes a little while or quenching is insufficient. In particular, smoke from the cigarette ends which are not thoroughly quenched in ashtrays equipped in the stations, trains, etc. often causes discomfort.

For resolving such discomfort, water may be put in ashtrays prior to use or after use. Nevertheless, since water vaporizes rather rapidly and in addition, cigarettes themselves absorb water, ashtrays get dry in a short time. Thus, if cigarettes in ashtrays are to be quenched with water, water must be frequently supplemented. Furthermore, once ashtrays get dry, it makes cleaning hard because the eluted substances and cigarette ashes would stick to the ashtrays.

Ingredients of cigarettes are eluted in water in ashtrays with lapse of time, and as a result, the water turns brown and generates unpleasant odors. Despite such situation, special means of deodorization is not generally taken.

In view of the foregoing situation, it is desired that quenching and deodorizing compositions for cigarettes satisfy the following quality requirements.

(1) They possess excellent quenching properties.
(2) They possess excellent deodorizing properties.
(3) Their quenching and deodorizing actions endure for a long time.
(4) Elution of cigarette ingredients is less.
(5) They hardly pollute the environment.
(6) They are less likely to spill from ashtrays even in shaky circumstances such as in trains, airplanes, or the like.
(7) They are capable of quenching a lot of cigarettes.
(8) Water evaporates little.
(9) Washing of ashtrays after use is easy.

The object of the present invention is to provide quenching and deodorizing compositions satisfying all the above requirements, particularly gel liquid quenching and deodorizing compositions for cigarettes.

SUMMARY OF THE INVENTION

The present inventors have conducted intensive researches and studies, and found that all the above-mentioned requirements are satisfied by compositions comprising water, a deodorizing agent, a water-absorbing polymer or thickener and a viscosity-imparting agent, specifically those comprising a water-absorbing polymer or thickener in a proportion of 0.1-100 parts by weight, a deodorizing agent in a proportion of 0.01-1 part by weight and a viscosity-imparting agent in a proportion of 1-40 parts by weight relative to 100 parts by weight of water, the viscosity of which at 25° C. is 300-1,000 cps when a water-absorbing polymer is used and 300-25,000 cps when a thickener is used. Further studies by the inventors resulted in the completion of the invention.

This invention provides the following.

(1) A gel liquid quenching and deodorizing composition for cigarettes, which comprises water, a deodorizing agent, a water-absorbing polymer or thickener and a viscosity-imparting agent.

(2) A gel liquid quenching and deodorizing composition for cigarettes, which comprises a water-absorbing polymer or thickener in a proportion of 0.1-100 parts by weight, a deodorizing agent in a proportion of 0.01-1 part by weight and a viscosity-imparting agent in a proportion of 1-40 parts by weight relative to 100 parts by weight of water, the viscosity of which at 25° C. is 300-1,000 cps when a water-absorbing polymer is used and 300-25,000 cps when a thickener is used.

DETAILED DESCRIPTION OF THE INVENTION

The water-absorbing polymer to be used in the present invention is macromolecular substances capable of absorbing water in an amount several dozens-fold to at least one thousand-fold their own weight. As such water-absorbing polymers, there may be mentioned resins which swell with water to form hydrogels but do not release water against pressure. Specifically, examples thereof include vinyl alcohol-acrylic acid copolymers, [e.g. Sumikagel S-50 (manufactured by Sumitomo Chemical Co., Ltd.)], polyacrylic acid polymers [e.g. SANWET IM-5000 (manufactured by Sanyo Chemical Industries, Ltd.), Sumigakel N-100 (manufactured by Sumitomo Chemical Co., Ltd.), Aquirekeep (manufactured by Seitetsu Kagaku Co., Ltd.), etc.], starch-acrylic acid block copolymers [e.g. SANWET IM-1000 (manufactured by Sanyo Chemical Industries, Ltd.], vinyl acetate-acrylic acid ester copolymer ketone compounds, polyvinyl alcohol-maleic anhydride copolymer crosslinking products, isobutylene-maleic acid copolymer crosslinking products, polyacrylonitrile graft polymer saponified products, and the like. Among the foregoing, vinyl alcohol-acrylic acid copolymers are particularly preferable in that water is rarely eliminated even by ultraviolet irradiation, and they are capable of absorbing water in an amount about 450-fold to 600-fold their own weight.

The thickener used in the present invention is water-soluble and capable of imparting a constant viscosity. Examples thereof include sodium carboxymethyl cellulose, calcium carboxymethyl cellulose, sodium alginate, propyleneglycol alginate, sodium caseinate, sodium chondroitin sulfate, calcium cellulose glycolate, sodium cellulose glycolate, sodium starch glycolate, sodium starch phosphate, sodium polyacrylate, gums such as xanthan gum and karaya gum, or the like.

Since the deodorizing agent to be contained in the quenching and deodorizing compositions of the present invention is used in the presence of water, the agent is required to exhibit a deodorizing effect even in the presence of water. As such deodorizing agents, there may be mentioned, for example, deodorizing agents which mask odors by their own fragrance, those which decompose the ingredients generating foul odors by their own oxidizing properties, those which neutralize the ingredients of foul odors by their own neutralizing properties, and the like. As the preferred deodorizing agents, there may be mentioned, for example, flavonoids (e.g. flavonoids as ingredients of teas, flavone, flavonol, flavanone, flavanonol), polyphenols (e.g. myricetin, tannin, catechin, etc.), water-extracts of roasted plant fiber substances (e.g. water-extract of roasted rice brans, water-extracts of roasted soybeans, etc.), cyclodextrin ($\alpha$, $\beta$, $\gamma$), enzymes, enzymatic secretion and enzyme-producing microorganisms (e.g. digestive enzymes such as amylase, protease, lipase and cellulase, bacteria and yeasts), phytoncide, various iron salts (e.g. iron sulfate such as ferrous sulfate, ferrous hydrochloride, etc.), copper salts (e.g. cupric sulfate, cuprous hydrochloride, etc.), and so on.

As the water-extracts of roasted plant fiber substances, preferred are, for example, those described in Japanese Patent Unexamined Publication (Kokai) No. 99560/1989. As the water-extracts of roasted plant fiber substances, preferably used are those comprising extracts with an organic solvent of water-extracts of roasted plant fiber substances as an active ingredient, which are exemplified by the following. That is, plant fiber substances such as degreased soybeans and degreased rice brans are roasted lightly at about 170°-230° C. for about 5 minutes to 1 hour, followed by addition of water in a 10-fold to 20-fold amount and boiling for about 5-80 minutes, after which the concentrated extracts are separated by filtration and further concentrated to a one-tenth to three-tenths volume under reduced pressure, or the water-extracts obtained by additional spray-dry to an extent where the water content is reduced to about 4%. The thus-obtained concentrated extracts are extracted with an organic solvent, and the residues are filtered to afford the deodorizing agents to be incorporated in the quenching and deodorizing compositions of the present invention. Examples of the organic solvent to be used for the extraction include lower alcohols such as methyl alcohol, ethyl alcohol, isopropyl alcohol, etc., benzene, chloroform, n-hexane, carbon tetrachloride, and so on.

As the viscosity-imparting agent to be incorporated in the quenching and deodorizing compositions of the present invention, there is no limitation imposed thereon as long as they are capable of increasing viscosity and enabling a long term use by raising the boiling point, which results in lowering of the drying rate of the compositions of the present invention. As such viscosity-imparting agents, there can be mentioned, for example, what is called holding agents exemplified by alkylene glycols such as propylene glycol, ethylene glycol and glycerol.

The gel liquid quenching and deodorizing compositions for cigarettes of the present invention can be produced by adding the above-mentioned deodorizing agent, water-absorbing polymer or thickener and viscosity-imparting agent to water.

The proportions of the respective ingredients to be incorporated in the above-mentioned quenching and deodorizing compositions are not limited, and they are selected suitably in accordance with the place of use and the way of use. For example, it is preferable to incorporate the water-absorbing polymer or thickener in a proportion of 0.1-100 parts by weight, preferably 0.5-10 parts by weight, the deodorizing agent in a proportion of 0.01-1 part by weight, preferably 0.05-0.1 part by weight and viscosity-imparting agent in a proportion of 1-40 parts by weight, preferably 2-10 parts by weight relative to 100 parts by weight of water. Where the water-absorbing polymer or thickener is incorporated in a proportion of less than 0.1 part by weight, water absorption is poor, while it is incorporated in a proportion of over 100 parts by weight, it becomes pasty which is inconvenient to handle. Where the deodorizing agent is incorporated in a proportion of over 1 part by weight, the odor of the agent itself becomes noticeable, while it is incorporated in a proportion of less than 0.01 part by weight, it fails to exhibit sufficient deodorizing effects. Also, where the viscosity-imparting agent is incorporated in a proportion of over 40 parts by weight, it lowers the water-absorbing capacity of the water-absorbing polymer and in some cases it becomes flammable depending on the ingredients contained therein, while it is incorporated in a proportion of less than 1 part by weight, it fails to display sufficient effects.

The quenching and deodorizing compositions of the present invention have a viscosity at 25° C. of 300-1,000 cps, preferably 550-800 cps when a water-absorbing polymer is used and 300-25,000 cps, preferably 3,000-5,000 cps, more preferably 4,000-5,000 cps when a thickener is used, which is measured by B-type viscometer (manufactured by Tokyo Keiki Co., Ltd.). When the viscosity is below the above range, the quenching and deodorizing composition gets dried rapidly, lacking durability, and when the viscosity is beyond the above range, the composition fails to exhibit sufficient quenching effects and is inconvenient to handle.

Optional addition of antiseptics, perfumes, coloring agents, and the like normally used for the quenching and deodorizing compositions of the present invention is conductable. The antiseptics are preferably easily dissolved in water and are odorless, which are exemplified by methyl p-hydroxybenzoate, ethyl p-hydroxybenzoate, sodium dehydroacetate, or the like.

Below, there are given examples of the production of the quenching and deodorizing compositions of the present invention and experimental examples for showing the water holding properties and deodorizing effects thereof to explain the present invention in further detail.

REFERENCE EXAMPLE 1

Degreased soybeans were roasted (light roast) at about 170° C. for 40 minutes while rotated in a rotary, after which the roasted beans and a 10-fold amount of water were boiled. Following 40 minutes' boiling (total heating time of 60-90 minutes), the mixture was separated by filtration to give a hot water-extract, which was concentrated under reduced pressure to the two-tenths volume. The thus-obtained concentrated extract was subjected to spray dry to an extent where the water content was about 4% and extracted with a 10-fold amount of 95% ethanol.

After the residue was filtrated, it was concentrated by distilling off the ethanol under reduced pressure to give the deodorizing ingredient of a deodorizing agent.

EXAMPLE 1

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 5 parts by weight of ethylene glycol, 0.01 part by weight of a perfume and 0.001 part by weight of a coloring matter, filtration was conducted. To the filtrate was added 1.3 parts by weight of Sumikagel S-50 to give the quenching and deodorizing composition, the viscosity of which at 25° C. was 310 cps.

EXAMPLE 2

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 7 parts by weight of ethylene glycol, 0.01 part by weight of a perfume and 0.001 part by weight of a coloring matter, filtration was conducted. To the filtrate was added 1.5 parts by weight of Sumikagel S-50 to give the quenching and deodorizing composition, the viscosity of which at 25° C. was 600 cps.

EXAMPLE 3

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 9 parts by weight of ethylene glycol, 0.01 part by weight of a perfume and 0.001 part by weight of a coloring matter, filtration was conducted. To the filtrate was added 1.7 parts by weight of Sumikagel S-50 to give the quenching and deodorizing composition, the viscosity of which at 25° C. was 980 cps.

EXAMPLE 4

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 10 parts by weight of ethylene glycol, 0.01 part by weight of a perfume and 0.001 part by weight of a coloring matter, filtration was conducted. To the filtrate was added 1.2 parts by weight of sodium carboxymethyl cellulose to give the quenching and deodorizing composition, the viscosity of which at 25° C. was 1500 cps.

EXAMPLE 5

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 10 parts by weight of ethylene glycol, 0.01 part by weight of a perfume and 0.001 part by weight of a coloring matter, filtration was conducted. To the filtrate was added 1.5 parts by weight of sodium carboxymethyl cellulose to give the quenching and deodorizing composition, the viscosity of which at 25° C. was 4500 cps.

EXAMPLE 6

To 0.2 part by weight of the concentrated extract as obtained in Reference Example 1, 100 parts by weight of water was added, and the mixture was stirred. Thereto was added 28 parts by weight of ethanol containing 0.19 part by weight of ethyl p-hydroxybenzoate as an antiseptic, and the mixture was stirred. After further addition of 10 parts by weight of ethylene glycol, 0.01 part by weight of a perfume and 0.001 part by weight of a coloring matter, filtration was conducted. To the filtrate was added 2.3 parts by weight of sodium carboxymethyl cellulose to give the quenching and deodorizing composition, the viscosity of which at 25° C. was 21,000 cps.

EXPERIMENTAL EXAMPLE 1

Tests for Water Holding Properties and Cleaning Ability

The quenching and deodorizing composition (20 ml) as obtained in Example 1–6 was preserved in a glass or aluminium cylindrical vessel at a depth of 0.3 cm and a surface area of 64.0 cm$^2$ under various conditions. The respective water holding properties (dryness) and easiness of cleaning are as shown in Table 1. In Table 1, "open" means that the vessel was openly exposed as ordinary ashtrays in rooms, etc. and "closed" means that the vessel had a lid like ashtrays used in trains.

TABLE 1

| Temperature (°C.) | Time (days) | Material of the vessel | Condition | Dryness Ex. 1 | Ex. 2 | Ex. 3 | Cleaning Ex. 1 | Ex. 2 | Ex. 3 | Dryness Ex. 4 | Ex. 5 | Ex. 6 | Cleaning Ex. 4 | Ex. 5 | Ex. 6 |
| --- | --- | --- | --- | --- | --- | --- | --- | --- | --- | --- | --- | --- | --- | --- | --- |
| room temp. | 20 | glass | open | − | − | − | E | E | E | + | + | − | D | D | E |
| room temp. | 20 | alminium | open | − | − | − | E | E | E | + | + | − | D | D | E |
| 30 | 20 | glass | open | + | − | − | E | E | E | ++ | + | + | E | D | D |
| 30 | 20 | alminium | open | + | − | − | E | E | E | ++ | + | + | E | D | D |
| 70 | 1 | glass | open | ++ | + | − | D | E | E | ++ | ++ | + | E | E | D |
| 70 | 1 | alminium | open | ++ | + | − | D | E | E | ++ | ++ | + | E | E | D |
| 90 | 1 | glass | open | ++ | ++ | ++ | D | D | D | ++ | ++ | ++ | E | E | E |
| 90 | 1 | alminium | open | ++ | ++ | ++ | D | D | D | ++ | ++ | ++ | E | E | E |
| 90 | 20 | glass | closed | + | − | − | E | E | E | + | − | − | D | E | E |
| 90 | 20 | alminium | closed | + | − | − | E | E | E | + | − | − | D | E | E |

Note:
− means not dried; + means half dried; ++ means completely dried to come off in a sheet; E means easy; and D means difficult

EXPERIMENTAL EXAMPLE 2

Tests for Deodorizing Effect

In a 20 ml-vial was put 1 g of the quenching and deodorizing composition of Example 1 or 5, and the vial was sealed. Therein was injected 2 μl of triethylamine (30%), an odor ingredient of cigarette ends, with a microcylinder. The vial was kept at 40° C., and the head space in the vial was subjected to gas chromatography (Shimazu Corporation Ltd.) 15, 30, 45 and 60 minutes later for measurement. The results are as shown in Table 2.

TABLE 2

|  | Blank (water) Peak area | quenching and deodorizing comp. of Ex. 1 Peak area | Deodorizing percent (%) | Blank (water) Peak area | quenching and deodorizing comp. of Ex. 5 Peak area | Deodorizing percent (%) |
| --- | --- | --- | --- | --- | --- | --- |
| 15 min. later | 69687 | 13679 | 80.4 | 64234 | 10207 | 84.1 |
| 30 min. later | 70547 | 13066 | 81.5 | 68278 | 9795 | 85.7 |
| 45 min. later | 71906 | 13124 | 81.7 | 70978 | 10028 | 85.9 |
| 60 min. later | 72983 | 13340 | 81.7 | 71058 | 10168 | 85.7 |

EXPERIMENTAL EXAMPLE 3

A plate (surface area of 64 cm$^2$) in which 10 g of the quenching and deodorizing composition of Example 1 or 5 was put was left in a sealed 7 l-glass container, and a fan was run (inside conditions of the container: 30° C., 50% wet). Therein was injected an odor substance from cigarette ends with a microcylinder. The residual odor substance was measured by an indicator tube (manufactured by GASTEC) 10, 20, 30 and 60 minutes after the injection. The results are as shown in Tables 3 and 4.

TABLE 3

| | Odor substance: trimethylamine (5 μl) | | | | | |
| --- | --- | --- | --- | --- | --- | --- |
|  | Blank (air) Odor (ppm) | quenching and deodorizing comp. of Ex. 1 Odor (ppm) | Deodorizing percent (%) | Blank (air) Odor (ppm) | quenching and deodorizing comp. of Ex. 5 Odor (ppm) | Deodorizing percent (%) |
| immediately after | 35.0 | 35.0 | 0 | 35.0 | 35.0 | 0 |
| 10 min. later | 32.0 | 12.0 | 62.5 | 32.0 | 10.0 | 68.8 |
| 20 min. later | 32.0 | 9.5 | 70.3 | 32.0 | 6.0 | 81.3 |
| 30 min. later | 31.0 | 7.5 | 75.8 | 31.0 | 4.0 | 87.1 |
| 60 min. later | 29.5 | 4.5 | 84.7 | 29.5 | 2.0 | 93.2 |

TABLE 4

| | Odor substance: ammonia (1 μl) | | | | | |
| --- | --- | --- | --- | --- | --- | --- |
|  | Blank (air) Odor (ppm) | quenching and deodorizing comp. of Ex. 1 Odor (ppm) | Deodorizing percent (%) | Blank (air) Odor (ppm) | quenching and deodorizing comp. of Ex. 5 Odor (ppm) | Deodorizing percent (%) |
| immediately after | 58.2 | 56.0 | 3.7 | 58.0 | 56.0 | 3.4 |
| 10 min. later | 44.4 | 9.0 | 79.7 | 45.0 | 10.5 | 76.7 |
| 20 min. later | 40.8 | 5.0 | 87.7 | 40.0 | 5.0 | 87.5 |
| 30 min. later | 39.6 | less than 2.5 | 93.7 | 39.0 | 3.5 | 91.0 |
| 60 min. later | 34.8 | less than 2.5 |  | 36.2 | less than 2.5 | 93.1< |

EXPERIMENTAL EXAMPLE 4

In a plate of a diameter of 9 cm was put 20 ml of the quenching and deodorizing composition from Example 1–6, and lit cigarettes (half length) and cigarette ashes were put down therein to count the number of the quenched cigarettes.

|  | Viscosity (cps) | Number of quenched cigarettes |
| --- | --- | --- |
| Ex. 1 | 310 | 40 |
| Ex. 2 | 600 | 30 |
| Ex. 3 | 980 | 22 |
| Ex. 4 | 1500 | 50 |
| Ex. 5 | 4600 | 42 |
| Ex. 6 | 21000 | 31 |

The quenching and deodorizing compositions of the present invention are capable of retaining excellent quenching properties in ashtrays for a longer period than water, as well as of removing nicotine odors which are peculiar to cigarette ends. Since the quenching and deodorizing compositions for cigarettes of the present invention are in the gel form in use, they hardly spill from ashtrays, making themselves suitable for use in bullet trains, airplanes and so on in addition to the use at home and in offices. Besides, they also facilitate cleaning after use, since the gel liquid envelopes the cigarette ends and cigarette ashes do not stick to ashtrays and foul odors are not generated. Thus, ashtrays can be cleaned easily only by inclining them and letting the content flow out. Moreover, the quenching and deodorizing compositions of the present invention permit less elution of cigarette ingredients and enable quenching of a number of cigarettes.

What is claimed is:

1. A method for quenching and deodorizing cigarettes, which comprises quenching and deodorizing cigarettes with a gel liquid containing water, a deodorizing agent, said deodorizing agent being an extract with an organic solvent of a water-extract of roasted plant fiber substances and wherein said viscosity-imparting agent is selected from the group consisting of propylene glycol, ethylene glycol and glycerol a water-absorbing polymer or thickener, and a viscosity-imparting agent.

2. A method for quenching and deodorizing cigarettes as claimed in claim 1, which comprises quenching and deodorizing cigarettes with a gel liquid containing a water-absorbing polymer or thickener in a proportion of 0.1–100 parts by weight, a deodorizing agent in a proportion of 0.01–1 part by weight and a viscosity-imparting agent in a proportion of 1–40 parts by weight relative to 100 parts by weight of water.

3. A method for quenching and deodorizing cigarettes as claimed in claim 1, wherein the viscosity of the gel liquid at 25° C. is 300–1,000 cps when a water-absorbing polymer is used, and 300–25,000 cps when a thickener is used.

4. A method for quenching and deodorizing cigarettes as claimed in claim 1, wherein the water-absorbing polymer is a vinyl alcohol-acrylic acid copolymer.

5. A method for quenching and deodorizing cigarettes as claimed in claim 1, wherein the thickener is sodium carboxymethyl cellulose.

6. A method for quenching and deodorizing cigarettes as claimed in claim 1, which comprises quenching and deodorizing cigarettes with a gel liquid containing an extract with an organic solvent of a water-extract of roasted plant fiber substances as an active ingredient.

7. A method for quenching and deodorizing cigarettes as claimed in claim 1, wherein the viscosity-imparting agent is an alkylene glycol.

* * * * *